US005834296A

United States Patent [19]
Iizuka et al.

[11] Patent Number: 5,834,296
[45] Date of Patent: Nov. 10, 1998

[54] BACILLUS STRAIN AND HARMFUL ORGANISM CONTROLLING AGENTS

[75] Inventors: Toshihiko Iizuka, Sapporo; Michito Tagawa, Shiraoka-machi; Satoshi Arai, Shiraoki-machi; Masatsugu Niizeki, Shiraoki-machi; Toshiro Miyake, Shiraoka-machi, all of Japan

[73] Assignee: Nissan Chemical Industries, Ltd., Tokyo, Japan

[21] Appl. No.: 880,685

[22] Filed: Jun. 23, 1997

Related U.S. Application Data

[62] Division of Ser. No. 542,921, Oct. 13, 1995.

[30] Foreign Application Priority Data

Oct. 14, 1994 [JP] Japan .................................. 6-276082

[51] Int. Cl.$^6$ ...................................................... C12N 1/20
[52] U.S. Cl. ........................................................... 435/252.5
[58] Field of Search ............................................ 435/252.5

[56] References Cited

FOREIGN PATENT DOCUMENTS 6-65292  3/1994  Japan .
WO 93/03154  2/1993  WIPO .
WO 94/05771  3/1994  WIPO .

OTHER PUBLICATIONS

Katsutoshi Ogiwara et al., "Nucleotide Sequence of the Gene Encoding Novel Data–Endotoxin from *Bacillus Thuringiensis* Serovar Japonesis Strain Buibui Specific to Scarabaeid Beetles", Current Microbiology, vol. 30, No. 4, pp. 227–235, Apr. 1995.

*Primary Examiner*—Robert A. Wax
*Assistant Examiner*—Gabriele E. Bugalsky
*Attorney, Agent, or Firm*—Oblon, Spivak, McClelland, Maier & Neustadt, P.C.

[57] ABSTRACT

A novel crystal protein as an effective ingredient in harmful organism controlling agents, *Bacillus thuringiensis* var. *japonensis* strain N141 producing the protein, and a gene coding for the protein. This novel strain produces an insecticidal crystal toxin and is useful for a harmful organism controlling agent.

1 Claim, 3 Drawing Sheets subsp. *japonensis* strain N141

BACILLUS STRAIN AND HARMFUL ORGANISM CONTROLLING AGENTS

This is a Division of application Ser. No. 08/542,921 filed on Oct. 13, 1995, now pending.

FIELD OF THE INVENTION

The present invention relates to novel *Bacillus thuringiensis* var. *japonensis* strain N141, hereinafter sometimes abbreviated as N141, an insecticidal crystal protein produced thereby, a gene coding for the protein, and a harmful organism controlling agent comprising the protein.

BACKGROUND OF THE INVENTION

*Bacillus thuringiensis*, hereinafter abbreviated as Bt, and crystalline toxic proteins produced thereby are very useful as microbial pesticides, which do not pollute the environment (Bt agents), particularly as insecticides against lepidopterous insect pests, and in practice have been widely used in the world.

Bt is a gram-positive bacilliform bacterium which produces a crystal protein at the sporulation stage in the end of the logarithmic growth phase. When orally taken into the mid-gut of an insect, the crystal protein will be subjected to alkaline and enzymatic activation in the digestive juice to show insecticidal activities accompanied with paralyses. However, the protein does not show any toxicity to mammals. The crystal proteins produced by Bt are generally of so-called diamond-shaped, bipyramidal or rhomboidal form. These crystal proteins are formed with endospores in the sporangium and released from the sporangium together with the endospores (Hannay, C. L.; Nature, 172, 1004 (1953)).

Bt has been classified on the basis of H-antigen according to the proposal by De Barjac and Bonefoi (Entomophaga, 7, 5–31 (1962)). A large number of subspecies have been found up to now.

The insecticidal activities of these strains are highly specific and may vary with subspecies. For example, it has been known that the subspecies *kurustaki* and *aizawai* show activities against lepidopterous insects while other subspecies *tenebrionis* and *japonensis buibui* are active against coleopterous insects.

In practice, however, each of strains belonging to the same subspecies has a different insecticidal activity spectrum. Some of lepidopterous pests may have acquired resistance to the Bt strain which showed an activity against the lepidopterous pests. Further, few strains have been reported which show an effective activity against coleopterous insects.

Thus, novel Bt agents would be desirable which are also effective against the lepidopterous pests having resistance to some known Bt agents. Also, there is a need for Bt agents having an activity against coleopterous insects.

SUMMARY OF THE INVENTION

The present inventors have found a novel strain producing a crystalline protein which has an excellent insecticidal activity against lepidopterous and coleopterous insects and attained the present invention.

Accordingly, the present invention is concerned with a novel strain N141 of *Bacillus thuringiensis* var. *japonensis* which has been originally deposited at National Institute of Bioscience and Human-Technology (NIBH), Agency of Industrial Science and Technology, Ministry of International Trade and Industry, Tsukuba, Japan on Oct. 6, 1994 under Accession Number FERM P-14576. This strain has been transferred to the deposit under Budapest Treaty conditions on Sep. 25, 1995 under Accession Number FERM BP-5241.

According to another aspect of the present invention, there is provided a harmful organism controlling agent comprising as a main ingredient an insecticidal crystal protein produced by N141, hereinafter abbreviated as N141 crystal protein. Further, the present invention provides a method of protecting a plant from damage caused by a pest which comprises applying the pest with the N141 crystal protein.

DESCRIPTION OF THE INVENTION

The novel strain N141 was isolated by a conventional method for isolating a bacterium of the genus *Bacillus* forming thermostable spores. Namely, a suspension of soil taken in Saitama, Japan was subjected to heat treatment at 50° to 90° C. and cultivated in a standard plating medium such as NB plate media to isolate the strain.

Features of the Novel Strain N141

Colony formation: An opaque white colony with an irregular border.

Cell morphology in the growth phase: Typical of Bt.

Serotype of H-antigen: 23, *japonensis*.

Figure 1:
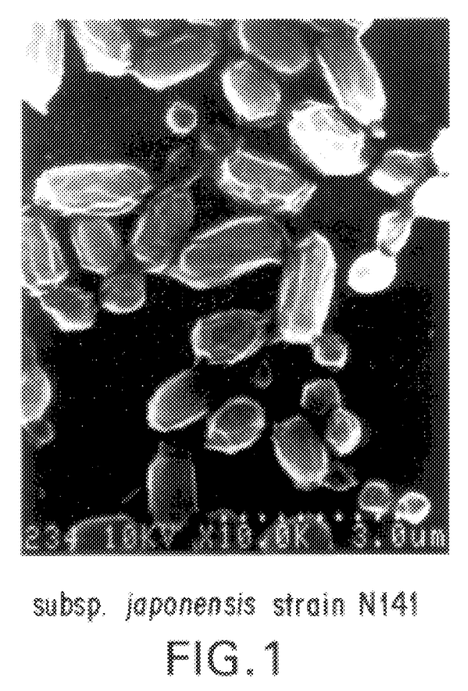
FIG. 1 is an electron microscopic photograph of *Bacillus thuringiensis* var. *japonensis* strain N141.

Intracellular component: A sporulating cell produces an amorphous crystal protein. The electron microscopic photograph of the crystal protein is shown in FIG. 1.

Alkali-soluble protein: This strain has a protein which runs to about 130,000 daltons on electrophoresis.

Activity: This strain has an insecticidal activity against lepidopterous and coleopterous pests tested.

Figure 2:
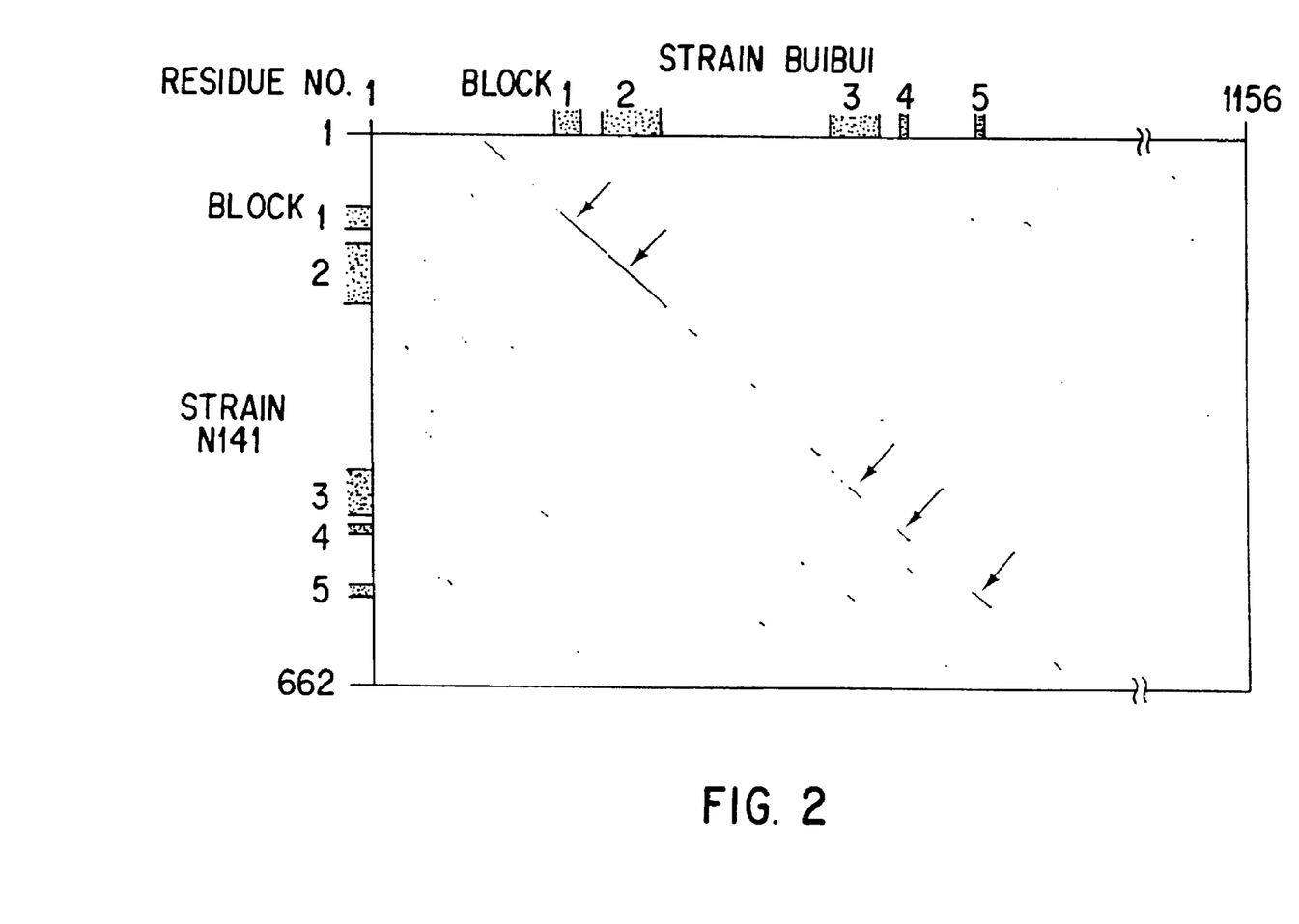
FIG. 2 shows a comparison of homology between the N-terminal 662 amino acids encoded by *Bacillus thuringiensis* var. *japonensis* N141 gene and the amino acid sequence encoded by *Bacillus thuringiensis buibui* gene.

Gene: Using antibodies raised by immunizing guinea pig with the crystal protein of about 130,000 daltons produced by this strain, screening was effected to clone a gene coding for the N141 crystal protein, hereinafter abbreviated as N141 gene. This gene has 3,759 bases and contains a translational region in from 47 to 3,556. Further, as compared with the known *japonensis buibui* gene having an activity against coleopterous insects (Japanese Patent Application Laying-open No. 65292/1994), this gene has only about 60% of homology in the amino acid sequence level with the known gene as shown in FIG. 2.

From these, the N141 of the present invention is distinguished from known strains and therefore is novel.

N141 strain may be cultivated using known standard media and fermentation methods. Carbon sources may include sucrose, maltose, glucose, fructose, molasses and soluble starch.

Nitrogen sources may include ammonium sulfate, ammonium chloride, cottonseed powder, yeast extract, soybean cake and casein hydrolysate. Minerals and vitamins may be supplied from organic carbon sources or nitrogen sources, such as molasses and yeast extract, and optionally inorganic salts and vitamins may be further added. The cultivation may preferably be carried out at a pH of 5 to 8 and a temperature of 25° to 30° C. for 2 to 5 days in a stirred and aerated system under aerobic conditions.

After cultivation, the insecticidal crystal protein may be isolated from the culture medium in a conventional manner such as centrifugation or filtration.

The N141 crystal protein may be employed as an active ingredient in a harmful organism controlling agent for use in controlling coleopterous and lepidopterous insects. However, the N141 strain itself may also be employed as a crystal toxin-containing ingredient without isolation of the crystalline protein.

When the crystal toxin-containing ingredient is used in a harmful organism controlling agent, it may generally be mixed with a suitable carrier, including a natural mineral fiber such as talc or kaolin, a solid carrier such as diatomaceous earth, or a liquid carrier such as water, and optionally an emulsifier, dispersant, suspending agent, penetrant, spreader and/or stabilizer may be added to formulate into any practical dosage form such as wettable powder, dust, granule or flowable agent.

Optionally, the agent may be formulated or sprayed together with other herbicide, pesticide, fungicide, plant growth-regulator, synergist, attractant, plant nutrient and/or fertilizer so long as they do not interfere with the crystalline toxin.

According to the present invention, the amount of the crystal toxin-containing ingredient applied may vary depending upon an application site, time and method, a pest to be controlled, and a crop to be protected; however, the amount of effective ingredient applied may usually about 0.1 to 99% by weight, preferably about 0.5 to 50% by weight of the agent.

Amounts of various ingredients in the agent of the present invention are exemplified below:

|  | Effective ingredient | Carrier | Surfactant | Auxiliary ingredients |
|---|---|---|---|---|
| Wettable powder | 1–70 | 15–93 | 3–10 | 0–5 |
| Dust | 0.01–30 | 67–99.5 |  | 0–3 |
| Granule | 0.01–30 | 67–99.5 |  | 0–8 |
| Flowable agent | 1–70 | 10–90 | 1–20 | 0–10 |

All the amounts shown in the above Table are % by weight.

When applied, a wettable powder or flowable agent is diluted with a predetermined amount of water before spraying while a dust or granule is directly sprayed without dilution with water.

Examples of each ingredient used in the agent may be as follows:
(Wettable powder)
Effective ingredient: the crystal toxin-containing material according to the present invention;
Carrier: calcium carbonate, kaolinite, Zeeklite D, Zeeklite PEP, diatomaceous earth, talc;
Surfactant: Sorpol, calcium lignin sulfonate, Lunox;
Other ingredients: Carplex # 80.
(Dust)
Effective ingredient: the crystal toxin-containing material according to the present invention;
Carrier: calcium carbonate, kaolinite, Zeeklite D, diatomaceous earth, talc;
Other ingredients: diisopropyl phosphate, Carplex # 80.
(Granule)
Effective ingredient: the crystal toxin-containing material according to the present invention;
Carrier: wheat flour, wheat bran, corn grits, Zeeklite D,
Other ingredients: paraffin, soybean oil.
(Flowable agent)
Effective ingredient: the crystal toxin-containing material according to the present invention;
Carrier: water;
Surfactant: Sorpol, sodium lignin sulfonate, Lunox, Nippol;
Other ingredients: ethylene glycol, propylene glycol.

Formulation examples of the harmful organism controlling agent comprising the crystal toxin-containing material according to the present invention as an effective ingredient are given below but the present invention is not limited thereto. All parts are by weight.

| Formulation Example 1: Wettable powder | |
|---|---|
| crystal toxin-containing material according to the present invention | 25 parts |
| Zeeklite PEP (mixture of kaolinite and sericite; Zeeklite Industry Co.; trade name) | 66 parts |
| Sorpol 5039 (anionic surfactant; Toho Chemical Co.; trade name) | 4 parts |
| Carplex #80 (white carbon; Shionogi Pharmaceutical Co.; trade name) | 3 parts |
| Calcium lignin sulfonate | 2 parts |

The above ingredients are homogeneously mixed and pulverized to yield a wettable powder.

Upon application, the wettable powder is diluted 500 to 2,000 times and sprayed so that the amount of crystal toxin-containing ingredient applied is 0.1 to 5 kg per hectare.

| Formulation Example 2: Dust | |
|---|---|
| crystal toxin-containing material according to the present invention | 3.0 parts |
| clay | 95 parts |
| diisopropyl phosphate | 1.5 parts |
| Carplex #80 (white carbon; Shionogi Pharmaceutical Co.; trade name) | 0.5 parts |

The above ingredients are homogeneously mixed and pulverized to yield a dust.

Upon application, the dust is sprayed so that the amount of crystal toxin-containing ingredient applied is 0.1 to 5 kg per hectare.

| Formulation Example 3: Flowable agent | |
|---|---|
| crystal toxin-containing material according to the present invention | 35 parts |
| Lunox 1000C (anionic surfactant; Toho Chemical Co.; trade name) | 0.5 part |
| Sorpol 3353 (nonionic surfactant; Toho Chemical Co.; trade name) | 10 part |
| 1% aqueous Xanthane gum solution (natural high polymer) | 20 part |
| water | 34.5 part |

The above ingredients except the crystal toxin-containing ingredient of the present invention are homogeneously dissolved, mixed with the crystal toxin-containing material, thoroughly stirred and wet-pulverized in a sand mill to yield a flowable agent.

Upon application, the flowable agent is diluted 50 to 2,000 times and sprayed so that the amount of crystal toxin-containing ingredient applied is 0.1 to 5 kg per hectare.

The method of protecting a plant from damage caused by lepidopterous and/or coleopterous pests according to the present invention generally comprises treating, e.g., by spraying, a plant infected or suspected to be infected with the pest, with the harmful organism controlling agent diluted with a diluent such as water. The effective ingredient of the controlling agent is a toxic δ-endotoxin. If desired, the toxic δ-endotoxin may be applied in an isolated form separately from a bacterium producing the toxin to the plant or infectious pest. Generally, however, it is not necessary to isolate the crystalline protein from the bacterium.

Pests which may be destroyed by the method of the present invention include insects of the order Lepidoptera or Coleoptera.

Lepidopterous insects may include armyworms, such as common cutworm (*Spodoptera litura*), beat armyworm (*Spodoptera exigua*) and cabbage armyworm (*Mamestra brassicae*); diamondback moth (*Plutella xylostella*), rice leafroller (*Cnaphalocrocis medinalis*), rice stem borer (*Chilo suppressalis*), rice skipper (*Parnara guttata*), common white (*Pieris rapae crucivora*), oriental moth (*Monema flavescens*) and common yellow swallowtail (*Papilio machaon hippocrates*).

Coleopterous insects may include grubs, such as cupreous chafer (*Anomala cuprea*), *Anomala schonfeldti,* soybean beetle (*Anomala rufocuprea*), Asiatic garden beetle (*Maladera castanea*), chestnut brown chafer (*Adoretus tenuimaculatus*) and Japanese beetle (*Popillia japonica*); lady beetles, such as 28-spotted ladybird (*Epilachna vigintioctopunctata*) and large 28-spotted ladybird (*Epilachna vigintioctomaculata*); weevils, such as rice water weevil (*Lissorhoptrus oryzophilus*), *Scepticus griseus,* sweetpotato weevil (*Cylas formicarius*), hunting billbug (*Sphenophrus venatus vestius*) and maize weevil (*Sitophilus zeamaise*); leaf beetles, such as striped flea beetle (*Phyllotreta striolata*) and cucurbit leaf beetle (*Aulacophora femoralis*); click beetles, such as *Melanotus okinawaensis;* longicorn beetles, such as Japanese pine sawer (*Monochamus alternatus*) and sesame-spotted longicorn beetle (*Mesosa myops*); bark beetles, such as Japanese bark beetle (*Scolytus japonicus*) and alnus ambrosia beetle (*Xylosandrus germanus*); flour beetles, such as yellow mealworm (*Tenebrio molitor*) and red flour beetle (*Tribolium castaneum*).

The method of the present invention may be used to protect a wide variety of plants which are subject to infection with lepidopterous or coleopterous insect pests. The plants to be protected by the method of the present invention include vegetables such as cabbage and cauliflower, fruit trees such as citrus and apples, grains such as rice, wheat and beans, stored grains, stored foods, lawn in golf courses and gardens, industrial crops such as tea and sugarcane, as well as flower. Also, trees in non-crop lands such as parks and forests.

N141 gene may be isolated from N141 strain. The whole DNA of N141 strain may be digested with one or more restriction enzymes and the resulting DNA fragments may be size-fractionated into DNA fractions of 2 to 5 Kbp. The fractions may be ligated to a suitable vector and used to transform *Escherichia coli.* A transformed *E. coli* possessing a desired gene may be identified by enzyme immunoassay using antibodies against the N141 crystal protein.

The N141-derived crystal protein gene DNA thus identified may be treated with a suitable restriction enzyme and the resulting DNA fragment is ligated to a suitable cloning vector to make a gene cassette.

The gene cassette may be used to transform a microorganism, such as *E. coli,* and the base sequence of N141 crystal gene may then be determined by gene analysis methods such as dideoxy method.

Further, the gene cassette may also be used to transform a gram-positive bacterium having an insecticidal activity, such as Bt. Thus, a transformed Bt may be produced which is effective to control a wider variety of insects.

To express the N141 gene in a plant, a suitable restriction site may be introduced into both sides of each gene or a portion thereof in the gene cassette. This may be carried out by site-directed mutagenesis.

The portion of N141 gene coding for an insecticidally effective portion of N141 protein may be inserted into the nuclear genome of a single plant cell in a stable manner and the thus transformed cells may be used to produce a transformed plant which is resistant to insects.

The thus transformed plant may be used to produce transformed plants having the same properties, or the insecticidally effective portion of N141 gene may be introduced into other varieties of the same or related plant species. A seed produced from the transformed plant contains the insecticidally effective portion of N141 gene as a stable genome insert.

The N141 strain may further be transformed with a foreign Bt gene having one or more insecticidal activities, whereby a transformed N141 strain may be produced which is useful for destroying a wider variety of pests.

The N141 crystal protein may be used to immunize guinea pig to prepare an antibody specific to this crystal protein.

In the protected area, i.e., in the area to which N141 strain and/or N141 crystal protein has been applied, certain insects will ingest the N141 strain and/or N141 crystal protein or mixture thereof, or transformed plants and/or microorganisms incorporating the N141 gene, and as a result they are killed or injured by the N141 crystal protein.

EXAMPLES

The present invention will be further illustrated by the following examples but is not limited thereto.

Example 1: Isolation and Properties of N141 Strain

N141 strain was isolated from soil taken in Saitama, Japan.

Ten mg of a soil sample was placed in an Erlenmeyer flask and 10 mL of sterilized water was injected thereinto. The flask was shaken for 30 minutes and allowed to stand for some time. Two mL of the supernatant was taken out and immediately heated at 80° C. for 10 minutes. The heated solution was then diluted in two steps, 10 times and 100 times, respectively. Each solution (1 mL) of the x10 and x100 diluted solutions was incubated on an NB plating medium (8.4 g NUTRIENT BROTH, 20 g agar per liter of sterilized water) at 30° C. for 24 to 48 hours.

Features of the Novel Strain N141

Colony formation: An opaque white colony with an irregular border.

Cell morphology in the growth phase: Typical of Bt.

Serotype of H-antigen: 23, *japonensis.*

Intracellular component: A sporulating cell produces an amorphous crystal protein. The electron microscopic photograph of the crystal protein is shown in FIG. 1.

Alkali-soluble protein: This strain has a protein which runs to about 130,000 daltons on electrophoresis.

Activity: This strain has an insecticidal activity against lepidopterous and coleopterous pests tested.

Gene: Using antibodies raised by immunizing guinea pig with the crystal protein of about 130,000 daltons produced by this strain, screening was effected to clone a gene coding for the N141 crystal protein, hereinafter abbreviated as N141 gene. This gene has 3,759 bases and contains a translational region in from 47 to 3,556. Further, as compared with the known *japonensis buibui* gene having an activity against coleopterous insects (Japanese Patent Application Laying-open No. 65292/1994), this gene has only about 60% of homology in the amino acid sequence level with the known gene as shown in FIG. 2.

Example 2: Storage and Sterilization of N141 Strain

Desirably, for longtime storage of N141 strain, N141 is subjected to rotary shaking culture with NB liquid medium (8.4 g NUTRIENT BROTH per liter of sterilized water) at 30° C. and 150–200 rpm for 24 to 72 hours and equal amounts of the culture medium and 30% glycerol are mixed and stored at −80° C., or alternatively, said culture medium is centrifuged and the resulting cells are suspended in a protective liquid (10% skim milk, 1% sodium glutamate) and dried under vacuum.

Sterilization of N141 strain is carried out in an autoclave at 120° C. for 20 minutes.

Example 3: Purification of Crystal Protein of N141 Strain

A platinum loopful of N141 strain was inoculated in a test tube containing 5 mL of NB liquid medium (8.4 g NUTRIENT BROTH per liter of sterilized water) and reciprocal shaking culture was carried out at 30° C. for 12 to 24 hours to yield a seed culture. The seed culture was inoculated in a 500 mL Erlenmeyer flask containing 100 ml of NB liquid medium (8.4 g NUTRIENT BROTH per liter of sterilized water) in a final concentration of 1% and shaking culture was effected at 30° C. and 150 rpm for 72 to 96 hours. Thereafter, cells, spores and crystal proteins were collected by centrifugation. A suitable amount of buffer (Tris-HCl, NaCl, EDTA) was added to the resulting precipitate and the mixture was subjected to ultrasonication to yield a suspension.

Example 4: Properties of N141 Crystal Protein

The suspension obtained in Example 3 was subjected to electrophoresis on 8% SDS-PAGE gel to investigate an electrophoretic pattern. Also, western blotting analysis was carried out using antibodies. As a result, it was revealed that N141 strain produces a crystal protein with a molecular weight of about 130,000 daltons.

Example 5: Insecticidal Activity of N141 Strain against Cupreous Chafer (*Anomala cuprea*)

The suspension prepared in Example 3 was diluted to a predetermined concentration and a spreader was added thereto. The thus prepared sample solution was mixed into leaf mould which had previously sterilized, and cupreous chafer (*Anomala cuprea*) was released. As a result of observation, an insecticidal activity against cupreous chafer (*Anomala cuprea*) was recognized.

Example 6: Insecticidal Activity of N141 Strain and N141 Crystal Protein against Diamondback Moth (*Plutella xylostella*)

The suspension prepared in Example 3 was diluted to a predetermined concentration and a spreader was added thereto to prepare a sample solution. A leaf of cabbage was immersed into the sample solution, air-dried thoroughly and placed into a styrol cup containing a wet filter paper. Larvae of diamondback moth (*Plutella xylostella*) in the middle of 3 larval instars stage were released into the cup and a mortality after 6 days was calculated from the following equation. The test was performed in 5-plicate with 5 larvae in each zone.

$$\text{Mortality (\%)} = \frac{\text{the number of dead insects}}{\text{the total number of insects}} \times 100$$

The results are shown in Table 1.

TABLE 1

Insecticidal activity of N141 strain and N141 crystal protein against larvae of diamondback moth (*Plutella xylostella*) in the middle of 3 larval instars stage

| Concentration (ppm) | Mortality (%) |
|---|---|
| 10000 | 100 |
| 3000 | 100 |
| 1000 | 100 |
| 100 | 50 |

Example 7: Insecticidal Activity of N141 Strain and N141 Crystal Protein against *Bombyx mori*

The suspension prepared in Example 3 was diluted to a predetermined concentration and a spreader was added thereto to prepare a sample solution. A leaf of mulberry was immersed into the sample solution, air-dried thoroughly and placed into a styrol cup containing a wet filter paper. Larvae of *Bombyx mori* on the second day of of 3 larval instars stage were released into the cup and a mortality after 6 days was calculated from the following equation. The test was performed in 5-plicate with 5 larvae in each zone.

$$\text{Mortality (\%)} = \frac{\text{the number of dead insects}}{\text{the total number of insects}} \times 100$$

The results are shown in Table 2.

TABLE 2

Insecticidal activity of N141 strain and N141 crystal protein against larvae of *Bombyx mori* on the second day of 3 larval instars stage

| Concentration (ppm) | Mortality (%) |
|---|---|
| 3000 | 100 |
| 1000 | 95 |
| 100 | 50 |

Example 8: Isolation of N141 Gene

The whole DNA was prepared from N141 strain and partially digested with EcoRI. The digested DNAs were fractionated and DNA fragments of about 2 to 5 Kbp were ligated to a phage vector λgt11 digested with EcoRI. These vectors were used to transform *E. coli*. The recombinant *E. coli* clones were screened with antibodies raised by immunizing guinea pig with about 130 kDa protein which was assumed to be N141 crystal protein, to identify clones containing N141 gene. DNAs were prepared from the identified recombinant *E. coli* clones and digested with restriction enzyme EcoRI. The digested DNA fragments were subjected to electrophoresis on 0.8% agarose gel to identify an inserted DNA fragment of about 3.4 Kbp.

Example 9: Cloning of N141 Gene

Figure 3:
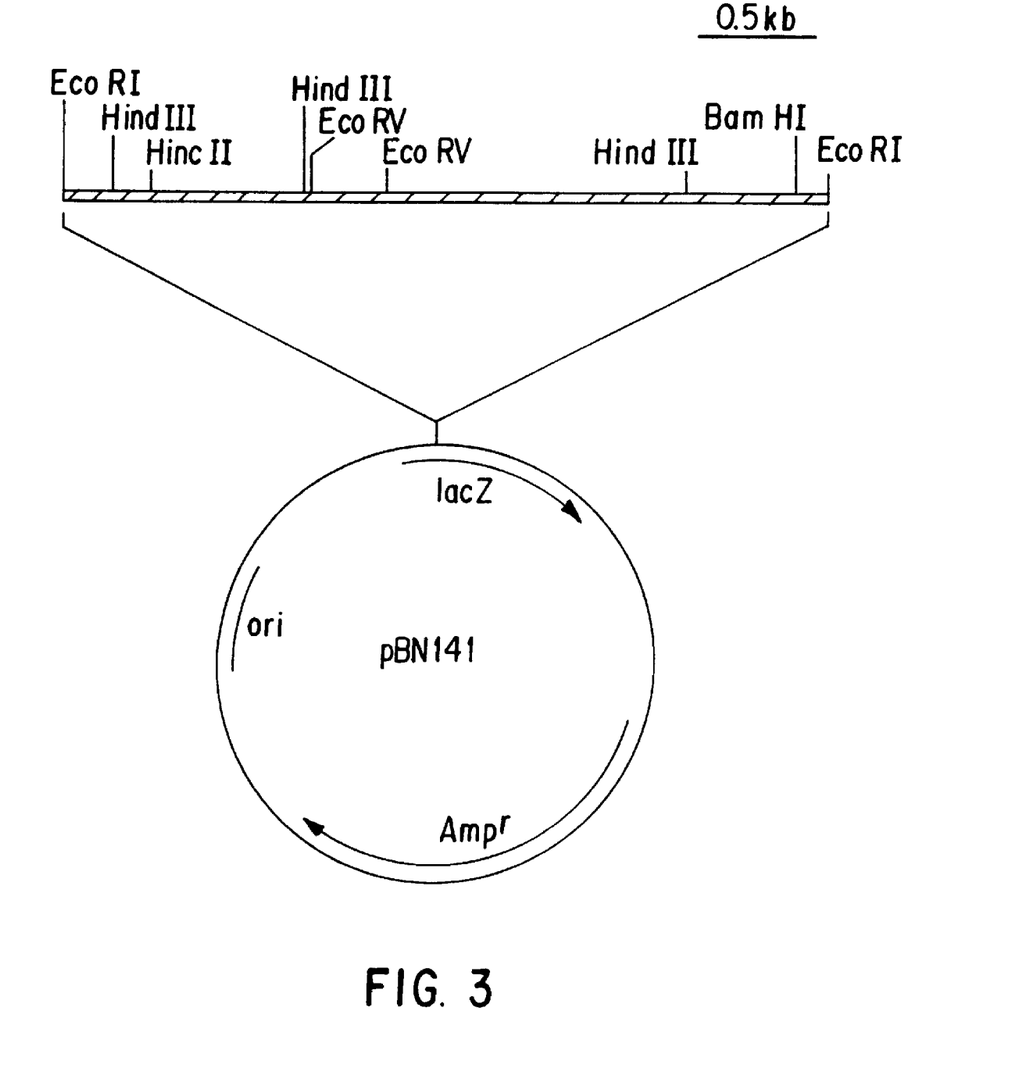
FIG. 3 depicts the cassette pBN141 comprising *Bacillus thuringiensis* var. *japonensis* N141 gene inserted into a vector.

The DNA fragments prepared in Example 8 were fractionated and ligated to a plasmid vector Bluescript II SK (−) digested with EcoRI so as to construct a gene cassette (pBN141; FIG. 3). This pBN141 was not of full length and cloning was again repeated. The base sequence of a DNA fragment containing a full length N141 gene was determined by the dideoxy method.

Example 10: Base and Amino Acid Sequences of N141 Gene

The base sequence consisted of 3759 bases as shown in SEQ ID NO:1. The open reading frame (ORF) consisted of 3510 bases, i.e. from 47th to 3556th bases, and coded for 1169 amino acids (the 1170th base being a termination codon). The amino acid sequence of the N-terminal 662 amino acids of this N141 protein was compared with those of a protein encoded by the known *japonensis buibui* gene which shows an activity against coleopterous insects (Japanese Patent Application Laying-open No. 65292/1994). It was found that the two genes had a homology in the amino acid level of only about 60% as shown in FIG. 2.

Example 11: Expression of N141 Crystal Protein in *E. coli* DH5α

To produce the crystal protein from N141 gene, the gene cassette pBN141 was used to transform *E. coli* DH5α. The resulting recombinant *E. coli,* hereinafter referred to *E. coli:* DH5α(pBN141), was incubated in LB-amp liquid medium (10 g Trypton, 10 g NaCl, 5 g Yeast extract, 0.2% glucose, 50 mg ampicillin per liter of sterilized water) at 37° C. for about 3 hours. IPTG was added to a final concentration of 1 mM and further incubated at 37° C. for 20 hours. After culture, the culture medium was centrifuged and 4 unit volumes of Lysis buffer were added to unit weight of the precipitate to suspend at room temperature for 10 hours. Then, Lysozyme was added and mixed in a final concentration of 1 mg/mL and allowed to stand on ice for 10 minutes. Further, Triton X-100 was added and mixed in a final concentration of 1% and allowed to stand at room temperature for 10 minutes. After centrifugation the supernatant was recovered.

Example 12: Properties of Protein Expressed in *E. coli:* DH5α (pBN141)

The supernatant obtained in Example 11 was subjected to electrophoresis on 8% SDS-PAGE gel and to western blotting using antibodies. As a result, it was confirmed that *E. coli:* DH5α (pBN141) produced N141 crystal protein.

Example 13: Insecticidal Activity of the Protein Expressed in *E. coli:* DH5α (pBN141) against Larvae of Diamondback Moth (*Plutella xylostella*)

To the supernatant solution obtained in Example 11, a spreader was added and diluted to prepare a sample solution. A leaf of cabbage was immersed into the sample solution, air-dried thoroughly and placed into a styrol cup containing a wet filter paper. Larvae of diamondback moth (*Plutella xylostella*) in the middle of 3 larval instars stage were released into the cup and a mortality after 6 days was calculated from the following equation. The test was performed in 5-plicate with 5 larvae in each zone.

$$\text{Mortality } (\%) = \frac{\text{the number of dead insects}}{\text{the total number of insects}} \times 100$$

The results are shown in Table 3.

TABLE 3

Insecticidai activity of the protein expressed in *E. coli*: DH5α (pBN141) against larvae of diamondback moth (*Plutella xylostella*) in the middle of 3 larval instars stage

| Concentration (ppm) | Mortality (%) |
| --- | --- |
| 200 | 85 |
| 100 | 50 |

Example 14: Insecticidal Activity of the Protein Expressed in *E. coli:* DH5α (pBN141) against Larvae of *Bombyx mori*

To the supernatant solution obtained in Example 11, a spreader was added and diluted to prepare a sample solution. A leaf of mulberry was immersed into the sample solution, air-dried thoroughly and placed into a styrol cup containing a wet filter paper. Larvae of *Bombyx mori* on the second day of of 3 larval instars stage were released into the cup and a mortality after 6 days was calculated from the following equation. The test was performed in 5-plicate with 5 larvae in each zone.

$$\text{Mortality } (\%) = \frac{\text{the number of dead insects}}{\text{the total number of insects}} \times 100$$

The results are shown in Table 4.

TABLE 4

Insecticidal activity of the protein expressed in *E. coli*: DH5α (pBN141) against larvae of *Bombyx mori* on the second day of 3 larval instars stage

| Concentration (ppm) | Mortality (%) |
| --- | --- |
| 200 | 70 |

While the above examples are directed to only several embodiments of the present invention, it is apparent to those skilled in the art that many other modifications and/or changes are contemplated in the present invention. For example, any peptide having an insecticidal activity and coding for an amino acid sequence which is different from that represented by SEQ ID NO:2 in that one or more amino acids may be added, deleted and/or replaced, as well as any DNA coding for such a modified peptide are included within the scope of the present invention.

The N141 crystal protein of the present invention has an activity not only against lepidopterous insects but also coleopterous insects such as cupreous chafer (*Anomala cuprea*) and is expected to be useful for insecticidal compositions.

What is claimed is:

1. *Bacillus thuringiensis* var. *japonensis* strain N141.

* * * * *

SEQUENCE LISTING ( 1 ) GENERAL INFORMATION:

( i i i ) NUMBER OF SEQUENCES: 2

( 2 ) INFORMATION FOR SEQ ID NO:1:

( i ) SEQUENCE CHARACTERISTICS:
        ( A ) LENGTH: 3759 base pairs
        ( B ) TYPE: nucleic acid
        ( C ) STRANDEDNESS: double (D) TOPOLOGY: linear (ii) MOLECULE TYPE: DNA (genomic)

(vi) ORIGINAL SOURCE:
  (A) ORGANISM: Bacillus thuringiensis var. japonensis
  (B) STRAIN: N141

(ix) FEATURE:
  (A) NAME/KEY: CDS
  (B) LOCATION: 47..3556

(xi) SEQUENCE DESCRIPTION: SEQ ID NO:1:

```
TTTTAAATAC ATTGGAGTGT AATAGACTGG TATTGGAGGA ACAAGT ATG AAT CGA              55
                                                 Met Asn Arg
                                                  1

AAT AAT CAA AAT GAA TAT GAA GTT ATT GAT GCC CCA CAT TGT GGG TGT            103
Asn Asn Gln Asn Glu Tyr Glu Val Ile Asp Ala Pro His Cys Gly Cys
     5              10                  15

CCG GCA GAT GAT GTT GTA AAA TAT CCT TTG ACA GAT GAT CCG AAT GCT            151
Pro Ala Asp Asp Val Val Lys Tyr Pro Leu Thr Asp Asp Pro Asn Ala
 20              25                  30                      35

GGA TTG CAA AAT ATG AAC TAT AAG GAA TAT TTA CAA ACG TAT GGT GGA            199
Gly Leu Gln Asn Met Asn Tyr Lys Glu Tyr Leu Gln Thr Tyr Gly Gly
             40              45                  50

GAC TAT ACA GAT CCT CTT ATT AAT CCT AAC TTA TCT GTT AGT GGA AAA            247
Asp Tyr Thr Asp Pro Leu Ile Asn Pro Asn Leu Ser Val Ser Gly Lys
         55              60                  65

GAT GTA ATA CAA GTT GGA ATT AAT ATT GTA GGG AGA TTA CTA AGC TTT            295
Asp Val Ile Gln Val Gly Ile Asn Ile Val Gly Arg Leu Leu Ser Phe
     70                  75                  80

TTT GGA TTC CCC TTT TCT AGT CAA TGG GTT ACT GTA TAT ACC TAT CTT            343
Phe Gly Phe Pro Phe Ser Ser Gln Trp Val Thr Val Tyr Thr Tyr Leu
 85                  90                  95

TTA AAC AGC TTG TGG CCG GAT GAC GAG AAT TCT GTA TGG GAC GCT TTT            391
Leu Asn Ser Leu Trp Pro Asp Asp Glu Asn Ser Val Trp Asp Ala Phe
100             105                 110                     115

ATG GAG AGA GTA GAA GAA CTT ATT GAT CAA AAA ATC TCA GAA GCA GTA            439
Met Glu Arg Val Glu Glu Leu Ile Asp Gln Lys Ile Ser Glu Ala Val
            120                 125                 130

AAG GGT AGG GCA TTG GAT GAC CTA ACT GGA TTA CAA TAT AAT TAT AAT            487
Lys Gly Arg Ala Leu Asp Asp Leu Thr Gly Leu Gln Tyr Asn Tyr Asn
            135                 140                 145

TTA TAT GTA GAA GCA TTA GAT GAG TGG CTG AAT AGA CCA AAT GGC GCA            535
Leu Tyr Val Glu Ala Leu Asp Glu Trp Leu Asn Arg Pro Asn Gly Ala
        150                 155                 160

AGG GCA TCC TTA GTT TCT CAG CGA TTT AAC ATT TTA GAT AGC CTA TTT            583
Arg Ala Ser Leu Val Ser Gln Arg Phe Asn Ile Leu Asp Ser Leu Phe
    165                 170                 175

ACA CAA TTT ATG CCA AGC TTT GGC TCT GGT CCT GGA AGT CAA AAT TAT            631
Thr Gln Phe Met Pro Ser Phe Gly Ser Gly Pro Gly Ser Gln Asn Tyr
180                 185                 190                 195

GCA ACT ATA TTA CTT CCA GTA TAT GCA CAA GCA GCA AAC CTT CAT TTG            679
Ala Thr Ile Leu Leu Pro Val Tyr Ala Gln Ala Ala Asn Leu His Leu
                200                 205                 210

TTA TTA TTA AAA GAT GCA GAC ATT TAT GGA GCT AGA TGG GGG CTG AAT            727
Leu Leu Leu Lys Asp Ala Asp Ile Tyr Gly Ala Arg Trp Gly Leu Asn
            215                 220                 225

CAA ACT CAA ATA GAT CAA TTC CAT TCT CGT CAA CAA AGC CTT ACT CAG            775
Gln Thr Gln Ile Asp Gln Phe His Ser Arg Gln Gln Ser Leu Thr Gln
            230                 235                 240

ACT TAT ACA AAT CAT TGT GTT ACT GCG TAT AAT GAT GGA TTA GCG GAA            823
Thr Tyr Thr Asn His Cys Val Thr Ala Tyr Asn Asp Gly Leu Ala Glu
```

```
                    245                             250                              255
TTA  AGA  GGC  ACA  ACC  GCT  GAG  AGT  TGG  TTT  AAA  TAC  AAT  CAA  TAT  CGT      871
Leu  Arg  Gly  Thr  Thr  Ala  Glu  Ser  Trp  Phe  Lys  Tyr  Asn  Gln  Tyr  Arg
260            Arg  Thr  265                 270                           275

AGA  GAA  ATG  ACT  TTG  ACG  GCA  ATG  GAT  TTA  GTG  GCA  TTA  TTC  CCA  TAT      919
Arg  Glu  Met  Thr  Leu  Thr  Ala  Met  Asp  Leu  Val  Ala  Leu  Phe  Pro  Tyr
                    280                 285                           290

TAT  AAT  TTA  CGA  CAA  TAT  CCA  GAT  GGG  ACA  AAT  CCT  CAA  CTT  ACA  CGT      967
Tyr  Asn  Leu  Arg  Gln  Tyr  Pro  Asp  Gly  Thr  Asn  Pro  Gln  Leu  Thr  Arg
               295                      300                           305

GAG  GTC  TAT  ACA  GAT  CCG  ATT  GCA  TTT  GAT  CCA  CTG  GAA  CAA  CCA  ACT     1015
Glu  Val  Tyr  Thr  Asp  Pro  Ile  Ala  Phe  Asp  Pro  Leu  Glu  Gln  Pro  Thr
          310                      315                 320

ACT  CAA  TTA  TGT  CGA  TCA  TGG  TAC  ATT  AAC  CCA  GCT  TTT  CGA  AAT  CAT     1063
Thr  Gln  Leu  Cys  Arg  Ser  Trp  Tyr  Ile  Asn  Pro  Ala  Phe  Arg  Asn  His
     325                      330                      335

TTG  AAT  TTC  TCT  GTA  CTA  GAA  AAT  TCA  TTG  ATT  CGT  CCC  CCG  CAC  CTT     1111
Leu  Asn  Phe  Ser  Val  Leu  Glu  Asn  Ser  Leu  Ile  Arg  Pro  Pro  His  Leu
340                      345                 350                           355

TTT  GAA  AGG  TTA  AGT  AAT  TTG  CAA  ATT  TTA  GTT  AAT  TAC  CAA  ACA  AAC     1159
Phe  Glu  Arg  Leu  Ser  Asn  Leu  Gln  Ile  Leu  Val  Asn  Tyr  Gln  Thr  Asn
                    360                 365                           370

GGT  AGC  GCT  TGG  CGT  GGG  TCA  AGG  GTA  AGA  TAC  CAT  TAT  TTG  CAT  AGT     1207
Gly  Ser  Ala  Trp  Arg  Gly  Ser  Arg  Val  Arg  Tyr  His  Tyr  Leu  His  Ser
               375                      380                 385

TCT  ATA  ATA  CAG  GAA  AAA  AGT  TAC  GGC  CTC  CTC  AGT  GAT  CCC  GTT  GGA     1255
Ser  Ile  Ile  Gln  Glu  Lys  Ser  Tyr  Gly  Leu  Leu  Ser  Asp  Pro  Val  Gly
               390                      395                 400

GCT  AAT  ATC  AAT  GTT  CAA  AAT  AAT  GAT  ATT  TAT  CAG  ATT  ATT  TCG  CAG     1303
Ala  Asn  Ile  Asn  Val  Gln  Asn  Asn  Asp  Ile  Tyr  Gln  Ile  Ile  Ser  Gln
405                      410                      415

GTT  AGC  AAT  TTT  GCT  AGT  CCT  GTT  GGC  TCA  TCA  TAT  AGT  GTT  TGG  GAC     1351
Val  Ser  Asn  Phe  Ala  Ser  Pro  Val  Gly  Ser  Ser  Tyr  Ser  Val  Trp  Asp
420                      425                 430                           435

ACT  AAC  TTT  TAT  TTG  AGT  TCA  GGA  CAA  GTA  AGT  GGG  ATT  TCA  GGA  TAT     1399
Thr  Asn  Phe  Tyr  Leu  Ser  Ser  Gly  Gln  Val  Ser  Gly  Ile  Ser  Gly  Tyr
               440                      445                           450

ACA  CAG  CAA  GGT  ATA  CCA  GCA  GTT  TGT  CTT  CAA  CAA  CGA  AAT  TCA  ACT     1447
Thr  Gln  Gln  Gly  Ile  Pro  Ala  Val  Cys  Leu  Gln  Gln  Arg  Asn  Ser  Thr
               455                      460                      465

GAT  GAG  TTA  CCA  AGC  TTA  AAT  CCG  GAA  GGA  GAT  ATC  ATT  AGA  AAT  TAT     1495
Asp  Glu  Leu  Pro  Ser  Leu  Asn  Pro  Glu  Gly  Asp  Ile  Ile  Arg  Asn  Tyr
          470                      475                      480

AGT  CAT  AGG  TTA  TCT  CAT  ATA  ACC  CAA  TAT  CGT  TTT  CAA  GCA  ACT  CAA     1543
Ser  His  Arg  Leu  Ser  His  Ile  Thr  Gln  Tyr  Arg  Phe  Gln  Ala  Thr  Gln
     485                      490                      495

AGT  GGT  AGT  CCA  TCA  ACT  GTT  AGC  GCA  AAT  TTA  CCT  ACT  TGT  GTA  TGG     1591
Ser  Gly  Ser  Pro  Ser  Thr  Val  Ser  Ala  Asn  Leu  Pro  Thr  Cys  Val  Trp
500                      505                      510                      515

ACG  CAT  CGA  GAT  GTG  GAC  CTT  GAT  AAT  ACC  ATT  ACT  GCG  AAT  CAA  ATT     1639
Thr  His  Arg  Asp  Val  Asp  Leu  Asp  Asn  Thr  Ile  Thr  Ala  Asn  Gln  Ile
               520                      525                      530

ACA  CAA  CTA  CCA  TTA  GTA  AAG  GCA  TAT  GAG  CTA  AGT  AGT  GGT  GCT  ACT     1687
Thr  Gln  Leu  Pro  Leu  Val  Lys  Ala  Tyr  Glu  Leu  Ser  Ser  Gly  Ala  Thr
               535                      540                      545

GTC  GTG  AAA  GGT  CCA  GGA  TTC  ACA  GGA  GGA  GAT  GTA  ATC  CGA  AGA  ACA     1735
Val  Val  Lys  Gly  Pro  Gly  Phe  Thr  Gly  Gly  Asp  Val  Ile  Arg  Arg  Thr
          550                      555                      560

AAT  ACT  GGT  GGA  TTC  GGA  GCA  ATA  AGG  GTG  TCG  GTC  ACT  GGA  CCG  CTA     1783
Asn  Thr  Gly  Gly  Phe  Gly  Ala  Ile  Arg  Val  Ser  Val  Thr  Gly  Pro  Leu
```

```
                    565                           570                           575
ACA  CAA  CGA  TAT  CGC  ATA  AGG  TTC  CGT  TAT  GCT  TCG  ACA  ATA  GAT  TTT     1831
Thr  Gln  Arg  Tyr  Arg  Ile  Arg  Phe  Arg  Tyr  Ala  Ser  Thr  Ile  Asp  Phe
580                      585                          590                     595

GAT  TTC  TTT  GTA  ACA  CGT  GGA  GGA  ACT  ACT  ATA  AAT  AAT  TTT  AGA  TTT     1879
Asp  Phe  Phe  Val  Thr  Arg  Gly  Gly  Thr  Thr  Ile  Asn  Asn  Phe  Arg  Phe
                    600                           605                          610

ACA  CGT  ACA  ATG  AAC  AGG  GGA  CAG  GAA  TCA  AGA  TAT  GAA  TCC  TAT  CGT     1927
Thr  Arg  Thr  Met  Asn  Arg  Gly  Gln  Glu  Ser  Arg  Tyr  Glu  Ser  Tyr  Arg
               615                      620                     625

ACT  GTA  GAG  TTT  ACA  ACT  CCT  TTT  AAC  TTT  ACA  CAA  AGT  CAA  GAT  ATA     1975
Thr  Val  Glu  Phe  Thr  Thr  Pro  Phe  Asn  Phe  Thr  Gln  Ser  Gln  Asp  Ile
          630                     635                          640

ATT  CGA  ACA  TCT  ATC  CAG  GGA  CTT  AGT  GGA  AAT  GGG  GAA  GTA  TAC  CTT     2023
Ile  Arg  Thr  Ser  Ile  Gln  Gly  Leu  Ser  Gly  Asn  Gly  Glu  Val  Tyr  Leu
     645                          650                          655

GAT  AGA  ATT  GAA  ATC  ATC  CCT  GTG  AAC  CCG  GCA  CGA  GAA  GCA  GAA  GAG     2071
Asp  Arg  Ile  Glu  Ile  Ile  Pro  Val  Asn  Pro  Ala  Arg  Glu  Ala  Glu  Glu
660                      665                          670                     675

GAT  TTA  GAA  GCA  GCG  AAG  AAA  GCG  GCT  AGG  CAG  AAC  TTG  TTT  ACA  CGT     2119
Asp  Leu  Glu  Ala  Ala  Lys  Lys  Ala  Ala  Arg  Gln  Asn  Leu  Phe  Thr  Arg
                    680                          685                          690

ACA  AGG  GAC  GGA  TTA  CAG  GTA  AAT  GTG  ACA  GAT  TAT  CAA  GTG  GAC  CAA     2167
Thr  Arg  Asp  Gly  Leu  Gln  Val  Asn  Val  Thr  Asp  Tyr  Gln  Val  Asp  Gln
               695                      700                     705

GCG  GCA  AAT  TTA  GTG  TCA  TGC  TTA  TCC  GAT  GAA  CAA  TAT  GGG  CAT  GAC     2215
Ala  Ala  Asn  Leu  Val  Ser  Cys  Leu  Ser  Asp  Glu  Gln  Tyr  Gly  His  Asp
          710                     715                          720

AAA  AAG  ATG  TTA  TTG  GAA  GCG  GTA  AGA  GCG  GCA  AAA  CGC  CTC  AGC  CGC     2263
Lys  Lys  Met  Leu  Leu  Glu  Ala  Val  Arg  Ala  Ala  Lys  Arg  Leu  Ser  Arg
     725                          730                          735

GAA  CGC  AAC  TTA  CTT  CAA  GAT  CCA  GAT  TTT  AAT  ACA  ATC  AAT  AGT  ACA     2311
Glu  Arg  Asn  Leu  Leu  Gln  Asp  Pro  Asp  Phe  Asn  Thr  Ile  Asn  Ser  Thr
740                      745                          750                     755

GAA  GAG  AAT  GGC  TGG  AAG  GCA  AGT  AAC  GGT  GTT  ACT  ATT  AGC  GAG  GGC     2359
Glu  Glu  Asn  Gly  Trp  Lys  Ala  Ser  Asn  Gly  Val  Thr  Ile  Ser  Glu  Gly
                    760                          765                          770

GGT  CCA  TTC  TTT  AAA  GGT  CGT  GCA  CTT  CAG  TTA  GCA  AGC  GCA  AGA  GAA     2407
Gly  Pro  Phe  Phe  Lys  Gly  Arg  Ala  Leu  Gln  Leu  Ala  Ser  Ala  Arg  Glu
               775                      780                     785

AAT  TAT  CCA  ACA  TAC  ATT  TAT  CAA  AAA  GTA  GAT  GCA  TCG  GTG  TTA  AAG     2455
Asn  Tyr  Pro  Thr  Tyr  Ile  Tyr  Gln  Lys  Val  Asp  Ala  Ser  Val  Leu  Lys
          790                     795                          800

CCT  TAT  ACA  CGC  TAT  AGA  CTG  GAT  GGG  TTC  GTG  AAG  AGT  AGT  CAA  GAT     2503
Pro  Tyr  Thr  Arg  Tyr  Arg  Leu  Asp  Gly  Phe  Val  Lys  Ser  Ser  Gln  Asp
805                      810                          815

TTA  GAA  ATT  GAT  CTC  ATT  CAC  TAT  CAT  AAA  GTC  CAT  CTT  GTG  AAA  AAT     2551
Leu  Glu  Ile  Asp  Leu  Ile  His  Tyr  His  Lys  Val  His  Leu  Val  Lys  Asn
820                      825                          830                     835

GTA  CCA  GAT  AAT  TTA  GTA  TCC  GAT  ACT  TAC  TCG  GAT  GGT  TCT  TGC  AGT     2599
Val  Pro  Asp  Asn  Leu  Val  Ser  Asp  Thr  Tyr  Ser  Asp  Gly  Ser  Cys  Ser
                    840                          845                          850

GGA  ATG  AAT  CGA  TGT  GAG  GAA  CAA  CAG  ATG  GTA  AAT  GCG  CAA  CTG  GAA     2647
Gly  Met  Asn  Arg  Cys  Glu  Glu  Gln  Gln  Met  Val  Asn  Ala  Gln  Leu  Glu
               855                      860                     865

ACA  GAA  CAT  CAT  CAT  CCG  ATG  GAT  TGC  TGT  GAA  GCG  GCT  CAA  ACA  CAT     2695
Thr  Glu  His  His  His  Pro  Met  Asp  Cys  Cys  Glu  Ala  Ala  Gln  Thr  His
          870                     875                          880

GAG  TTT  TCT  TCC  TAT  ATT  AAT  ACA  GGG  GAT  CTA  AAT  GCA  AGT  GTA  GAT     2743
Glu  Phe  Ser  Ser  Tyr  Ile  Asn  Thr  Gly  Asp  Leu  Asn  Ala  Ser  Val  Asp
```

|  |  |  |  |  |  |  |  |  |  |  |  |  |  |  |  |
|---|---|---|---|---|---|---|---|---|---|---|---|---|---|---|---|
|  | 885 |  |  |  |  | 890 |  |  |  |  | 895 |  |  |  |  |
| CAG | GGC | ATT | TGG | GTT | GTA | TTA | AAA | GTT | CGA | ACA | ACA | GAT | GGG | TAT | GCG | 2791
| Gln | Gly | Ile | Trp | Val | Val | Leu | Lys | Val | Arg | Thr | Thr | Asp | Gly | Tyr | Ala |
| 900 |  |  |  |  | 905 |  |  |  |  | 910 |  |  |  |  | 915 |

| ACG | TTA | GGA | AAT | CTT | GAA | TTG | GTA | GAG | GTT | GGG | CCA | TTA | TCG | GGT | GAA | 2839
|---|---|---|---|---|---|---|---|---|---|---|---|---|---|---|---|
| Thr | Leu | Gly | Asn | Leu | Glu | Leu | Val | Glu | Val | Gly | Pro | Leu | Ser | Gly | Glu |
|  |  |  |  | 920 |  |  |  |  | 925 |  |  |  |  | 930 |  |

| TCT | CTA | GAA | CGG | GAA | CAA | AGA | GAT | AAT | GCG | AAA | TGG | AAT | GCA | GAG | CTA | 2887
|---|---|---|---|---|---|---|---|---|---|---|---|---|---|---|---|
| Ser | Leu | Glu | Arg | Glu | Gln | Arg | Asp | Asn | Ala | Lys | Trp | Asn | Ala | Glu | Leu |
|  |  |  | 935 |  |  |  |  | 940 |  |  |  |  | 945 |  |  |

| GGA | AGA | AAA | CGT | GCA | GAA | ATA | GAT | CGT | GTG | TAT | TTA | GCT | GCG | AAA | CAA | 2935
|---|---|---|---|---|---|---|---|---|---|---|---|---|---|---|---|
| Gly | Arg | Lys | Arg | Ala | Glu | Ile | Asp | Arg | Val | Tyr | Leu | Ala | Ala | Lys | Gln |
|  |  | 950 |  |  |  |  | 955 |  |  |  |  | 960 |  |  |  |

| GCA | ATT | AAT | CAT | CTG | TTT | GTA | GAC | TAT | CAA | GAT | CAA | CAA | TTA | AAT | CCA | 2983
|---|---|---|---|---|---|---|---|---|---|---|---|---|---|---|---|
| Ala | Ile | Asn | His | Leu | Phe | Val | Asp | Tyr | Gln | Asp | Gln | Gln | Leu | Asn | Pro |
|  | 965 |  |  |  |  | 970 |  |  |  |  | 975 |  |  |  |  |

| GAA | ATT | GGG | CTA | GCA | GAA | ATT | AAT | GAA | GCT | TCA | AAT | CTT | GTA | GAG | TCA | 3031
|---|---|---|---|---|---|---|---|---|---|---|---|---|---|---|---|
| Glu | Ile | Gly | Leu | Ala | Glu | Ile | Asn | Glu | Ala | Ser | Asn | Leu | Val | Glu | Ser |
| 980 |  |  |  |  | 985 |  |  |  |  | 990 |  |  |  |  | 995 |

| ATT | TCG | GGT | GTA | TAT | AGT | GAT | ACA | CTA | TTA | CAG | ATT | CCT | GGG | ATT | AAC | 3079
|---|---|---|---|---|---|---|---|---|---|---|---|---|---|---|---|
| Ile | Ser | Gly | Val | Tyr | Ser | Asp | Thr | Leu | Leu | Gln | Ile | Pro | Gly | Ile | Asn |
|  |  |  | 1000 |  |  |  |  | 1005 |  |  |  |  | 1010 |  |  |

| TAC | GAA | ATT | TAC | ACA | GAG | TTA | TCC | GAT | CGC | TTA | CAA | CAA | GCA | TCG | TAT | 3127
|---|---|---|---|---|---|---|---|---|---|---|---|---|---|---|---|
| Tyr | Glu | Ile | Tyr | Thr | Glu | Leu | Ser | Asp | Arg | Leu | Gln | Gln | Ala | Ser | Tyr |
|  |  | 1015 |  |  |  |  | 1020 |  |  |  |  | 1025 |  |  |  |

| CTG | TAT | ACG | TCT | CGA | AAT | GCG | GTG | CAA | AAT | GGA | GAC | TTT | AAC | AGT | GGT | 3175
|---|---|---|---|---|---|---|---|---|---|---|---|---|---|---|---|
| Leu | Tyr | Thr | Ser | Arg | Asn | Ala | Val | Gln | Asn | Gly | Asp | Phe | Asn | Ser | Gly |
|  |  | 1030 |  |  |  |  | 1035 |  |  |  |  | 1040 |  |  |  |

| CTA | GAT | AGT | TGG | AAT | ACA | ACT | ACG | GAT | GCA | TCG | GTT | CAG | CAA | GAT | GGC | 3223
|---|---|---|---|---|---|---|---|---|---|---|---|---|---|---|---|
| Leu | Asp | Ser | Trp | Asn | Thr | Thr | Thr | Asp | Ala | Ser | Val | Gln | Gln | Asp | Gly |
|  |  | 1045 |  |  |  |  | 1050 |  |  |  |  | 1055 |  |  |  |

| AAT | ATG | CAT | TTC | TTA | GTT | CTT | TCG | CAT | TGG | GAT | GCA | CAA | GTT | TCT | CAA | 3271
|---|---|---|---|---|---|---|---|---|---|---|---|---|---|---|---|
| Asn | Met | His | Phe | Leu | Val | Leu | Ser | His | Trp | Asp | Ala | Gln | Val | Ser | Gln |
| 1060 |  |  |  |  | 1065 |  |  |  |  | 1070 |  |  |  |  | 1075 |

| CAA | TTG | AGA | GTA | AAT | CCG | AAT | TGT | AAG | TAT | GTC | TTA | CGT | GTG | ACA | GCA | 3319
|---|---|---|---|---|---|---|---|---|---|---|---|---|---|---|---|
| Gln | Leu | Arg | Val | Asn | Pro | Asn | Cys | Lys | Tyr | Val | Leu | Arg | Val | Thr | Ala |
|  |  |  |  | 1080 |  |  |  |  | 1085 |  |  |  |  | 1090 |  |

| AGA | AAA | GTA | GGA | GGC | GGA | GAT | GGA | TAC | GTC | ACA | ATC | CGA | GAT | GGC | GCT | 3367
|---|---|---|---|---|---|---|---|---|---|---|---|---|---|---|---|
| Arg | Lys | Val | Gly | Gly | Gly | Asp | Gly | Tyr | Val | Thr | Ile | Arg | Asp | Gly | Ala |
|  |  | 1095 |  |  |  |  | 1100 |  |  |  |  | 1105 |  |  |  |

| CAT | CAC | CAA | GAA | ACT | CTT | ACA | TTT | AAT | GCA | TGT | GAC | TAC | GAT | GTA | AAT | 3415
|---|---|---|---|---|---|---|---|---|---|---|---|---|---|---|---|
| His | His | Gln | Glu | Thr | Leu | Thr | Phe | Asn | Ala | Cys | Asp | Tyr | Asp | Val | Asn |
|  |  |  | 1110 |  |  |  |  | 1115 |  |  |  |  | 1120 |  |  |

| GGT | ACG | TAT | GTC | AAT | GAC | AAT | TCG | TAT | ATA | ACA | GAA | GAA | GTG | GTA | TTC | 3463
|---|---|---|---|---|---|---|---|---|---|---|---|---|---|---|---|
| Gly | Thr | Tyr | Val | Asn | Asp | Asn | Ser | Tyr | Ile | Thr | Glu | Glu | Val | Val | Phe |
|  | 1125 |  |  |  |  | 1130 |  |  |  |  | 1135 |  |  |  |  |

| TAC | CCA | GAG | ACA | AAA | CAT | ATG | TGG | GTA | GAG | GTG | AGT | GAA | TCC | GAA | GGT | 3511
|---|---|---|---|---|---|---|---|---|---|---|---|---|---|---|---|
| Tyr | Pro | Glu | Thr | Lys | His | Met | Trp | Val | Glu | Val | Ser | Glu | Ser | Glu | Gly |
| 1140 |  |  |  |  | 1145 |  |  |  |  | 1150 |  |  |  |  | 1155 |

| TCA | TTC | TAT | ATA | GAC | AGT | ATT | GAG | TTT | ATT | GAA | ACA | CAA | GAG | TAG |  | 3556
|---|---|---|---|---|---|---|---|---|---|---|---|---|---|---|---|
| Ser | Phe | Tyr | Ile | Asp | Ser | Ile | Glu | Phe | Ile | Glu | Thr | Gln | Glu | * |  |
|  |  |  | 1160 |  |  |  |  | 1165 |  |  |  |  | 1170 |  |  |

```
AAGAGGGGGA TCCTAACGTA TAGCAACTAT GAGAGGATAC TCCGTACAAA CAAAGATTAA    3616

AAAAAGGTAA AATGAATAGA ACCCCCTACT GGTAGAAGGT CTGGTAGGGG GTTCTTACAT    3676

GAAAAAATGT AGCTGTTTAC TAAGGTATAT AAAAAACAGC ATATTTGATA GAAAAAAATG    3736

AGTACCTTAT AAAGAAAGAA TTC                                          3759
```

( 2 ) INFORMATION FOR SEQ ID NO:2:

( i ) SEQUENCE CHARACTERISTICS:
  ( A ) LENGTH: 1169 amino acids
  ( B ) TYPE: amino acid
  ( D ) TOPOLOGY: linear ( i i ) MOLECULE TYPE: protein ( x i ) SEQUENCE DESCRIPTION: SEQ ID NO:2:

```
Met Asn Arg Asn Asn Gln Asn Glu Tyr Glu Val Ile Asp Ala Pro His
  1               5                  10                  15

Cys Gly Cys Pro Ala Asp Asp Val Val Lys Tyr Pro Leu Thr Asp Asp
             20                  25                  30

Pro Asn Ala Gly Leu Gln Asn Met Asn Tyr Lys Glu Tyr Leu Gln Thr
         35                  40                  45

Tyr Gly Gly Asp Tyr Thr Asp Pro Leu Ile Asn Pro Asn Leu Ser Val
     50                  55                  60

Ser Gly Lys Asp Val Ile Gln Val Gly Ile Asn Ile Val Gly Arg Leu
 65                  70                  75                  80

Leu Ser Phe Phe Gly Phe Pro Phe Ser Ser Gln Trp Val Thr Val Tyr
                 85                  90                  95

Thr Tyr Leu Leu Asn Ser Leu Trp Pro Asp Asp Glu Asn Ser Val Trp
             100                 105                 110

Asp Ala Phe Met Glu Arg Val Glu Leu Ile Asp Gln Lys Ile Ser
             115                 120                 125

Glu Ala Val Lys Gly Arg Ala Leu Asp Asp Leu Thr Gly Leu Gln Tyr
        130                 135                 140

Asn Tyr Asn Leu Tyr Val Glu Ala Leu Asp Glu Trp Leu Asn Arg Pro
145                 150                 155                 160

Asn Gly Ala Arg Ala Ser Leu Val Ser Gln Arg Phe Asn Ile Leu Asp
                165                 170                 175

Ser Leu Phe Thr Gln Phe Met Pro Ser Phe Gly Ser Gly Pro Gly Ser
                180                 185                 190

Gln Asn Tyr Ala Thr Ile Leu Leu Pro Val Tyr Ala Gln Ala Ala Asn
            195                 200                 205

Leu His Leu Leu Leu Leu Lys Asp Ala Asp Ile Tyr Gly Ala Arg Trp
    210                 215                 220

Gly Leu Asn Gln Thr Gln Ile Asp Gln Phe His Ser Arg Gln Gln Ser
225                 230                 235                 240

Leu Thr Gln Thr Tyr Thr Asn His Cys Val Thr Ala Tyr Asn Asp Gly
                245                 250                 255

Leu Ala Glu Leu Arg Gly Thr Thr Ala Glu Ser Trp Phe Lys Tyr Asn
            260                 265                 270

Gln Tyr Arg Arg Glu Met Thr Leu Thr Ala Met Asp Leu Val Ala Leu
        275                 280                 285

Phe Pro Tyr Tyr Asn Leu Arg Gln Tyr Pro Asp Gly Thr Asn Pro Gln
    290                 295                 300

Leu Thr Arg Glu Val Tyr Thr Asp Pro Ile Ala Phe Asp Pro Leu Glu
305                 310                 315                 320

Gln Pro Thr Thr Gln Leu Cys Arg Ser Trp Tyr Ile Asn Pro Ala Phe
                325                 330                 335

Arg Asn His Leu Asn Phe Ser Val Leu Glu Asn Ser Leu Ile Arg Pro
            340                 345                 350

Pro His Leu Phe Glu Arg Leu Ser Asn Leu Gln Ile Leu Val Asn Tyr
        355                 360                 365

Gln Thr Asn Gly Ser Ala Trp Arg Gly Ser Arg Val Arg Tyr His Tyr
```

|     |     | 370 |     |     |     | 375 |     |     |     | 380 |     |     |     |
|-----|-----|-----|-----|-----|-----|-----|-----|-----|-----|-----|-----|-----|-----|

Leu His Ser Ser Ile Ile Gln Glu Lys Ser Tyr Gly Leu Leu Ser Asp
385                     390                 395                 400

Pro Val Gly Ala Asn Ile Asn Val Gln Asn Asn Asp Ile Tyr Gln Ile
                405                 410                 415

Ile Ser Gln Val Ser Asn Phe Ala Ser Pro Val Gly Ser Ser Tyr Ser
            420                 425                 430

Val Trp Asp Thr Asn Phe Tyr Leu Ser Ser Gly Gln Val Ser Gly Ile
        435                 440                 445

Ser Gly Tyr Thr Gln Gln Gly Ile Pro Ala Val Cys Leu Gln Gln Arg
    450                 455                 460

Asn Ser Thr Asp Glu Leu Pro Ser Leu Asn Pro Glu Gly Asp Ile Ile
465                 470                 475                 480

Arg Asn Tyr Ser His Arg Leu Ser His Ile Thr Gln Tyr Arg Phe Gln
            485                 490                 495

Ala Thr Gln Ser Gly Ser Pro Ser Thr Val Ser Ala Asn Leu Pro Thr
        500                 505                 510

Cys Val Trp Thr His Arg Asp Val Asp Leu Asp Asn Thr Ile Thr Ala
        515                 520                 525

Asn Gln Ile Thr Gln Leu Pro Leu Val Lys Ala Tyr Glu Leu Ser Ser
530                 535                 540

Gly Ala Thr Val Val Lys Gly Pro Gly Phe Thr Gly Gly Asp Val Ile
545                 550                 555                 560

Arg Arg Thr Asn Thr Gly Gly Phe Gly Ala Ile Arg Val Ser Val Thr
            565                 570                 575

Gly Pro Leu Thr Gln Arg Tyr Arg Ile Arg Phe Arg Tyr Ala Ser Thr
        580                 585                 590

Ile Asp Phe Asp Phe Phe Val Thr Arg Gly Gly Thr Thr Ile Asn Asn
        595                 600                 605

Phe Arg Phe Thr Arg Thr Met Asn Arg Gly Gln Glu Ser Arg Tyr Glu
    610                 615                 620

Ser Tyr Arg Thr Val Glu Phe Thr Thr Pro Phe Asn Phe Thr Gln Ser
625                 630                 635                 640

Gln Asp Ile Ile Arg Thr Ser Ile Gln Gly Leu Ser Gly Asn Gly Glu
                645                 650                 655

Val Tyr Leu Asp Arg Ile Glu Ile Ile Pro Val Asn Pro Ala Arg Glu
            660                 665                 670

Ala Glu Glu Asp Leu Glu Ala Ala Lys Lys Ala Ala Arg Gln Asn Leu
        675                 680                 685

Phe Thr Arg Thr Arg Asp Gly Leu Gln Val Asn Val Thr Asp Tyr Gln
    690                 695                 700

Val Asp Gln Ala Ala Asn Leu Val Ser Cys Leu Ser Asp Glu Gln Tyr
705                 710                 715                 720

Gly His Asp Lys Lys Met Leu Leu Glu Ala Val Arg Ala Ala Lys Arg
                725                 730                 735

Leu Ser Arg Glu Arg Asn Leu Leu Gln Asp Pro Asp Phe Asn Thr Ile
            740                 745                 750

Asn Ser Thr Glu Glu Asn Gly Trp Lys Ala Ser Asn Gly Val Thr Ile
        755                 760                 765

Ser Glu Gly Gly Pro Phe Phe Lys Gly Arg Ala Leu Gln Leu Ala Ser
    770                 775                 780

Ala Arg Glu Asn Tyr Pro Thr Tyr Ile Tyr Gln Lys Val Asp Ala Ser
785                 790                 795                 800

-continued

```
Val  Leu  Lys  Pro  Tyr  Thr  Arg  Tyr  Arg  Leu  Asp  Gly  Phe  Val  Lys  Ser
               805                 810                           815

Ser  Gln  Asp  Leu  Glu  Ile  Asp  Leu  Ile  His  Tyr  His  Lys  Val  His  Leu
               820                 825                           830

Val  Lys  Asn  Val  Pro  Asp  Asn  Leu  Val  Ser  Asp  Thr  Tyr  Ser  Asp  Gly
          835                      840                 845

Ser  Cys  Ser  Gly  Met  Asn  Arg  Cys  Glu  Glu  Gln  Met  Val  Asn  Ala
     850                      855                 860

Gln  Leu  Glu  Thr  Glu  His  His  His  Pro  Met  Asp  Cys  Cys  Glu  Ala  Ala
865                      870                 875                           880

Gln  Thr  His  Glu  Phe  Ser  Ser  Tyr  Ile  Asn  Thr  Gly  Asp  Leu  Asn  Ala
                    885                 890                                895

Ser  Val  Asp  Gln  Gly  Ile  Trp  Val  Val  Leu  Lys  Val  Arg  Thr  Thr  Asp
               900                 905                      910

Gly  Tyr  Ala  Thr  Leu  Gly  Asn  Leu  Glu  Leu  Val  Glu  Val  Gly  Pro  Leu
          915                      920                 925

Ser  Gly  Glu  Ser  Leu  Glu  Arg  Glu  Gln  Arg  Asp  Asn  Ala  Lys  Trp  Asn
     930                      935                 940

Ala  Glu  Leu  Gly  Arg  Lys  Arg  Ala  Glu  Ile  Asp  Arg  Val  Tyr  Leu  Ala
945                 950                      955                           960

Ala  Lys  Gln  Ala  Ile  Asn  His  Leu  Phe  Val  Asp  Tyr  Gln  Asp  Gln  Gln
               965                 970                      975

Leu  Asn  Pro  Glu  Ile  Gly  Leu  Ala  Glu  Ile  Asn  Glu  Ala  Ser  Asn  Leu
               980                 985                      990

Val  Glu  Ser  Ile  Ser  Gly  Val  Tyr  Ser  Asp  Thr  Leu  Leu  Gln  Ile  Pro
               995                 1000                1005

Gly  Ile  Asn  Tyr  Glu  Ile  Tyr  Thr  Glu  Leu  Ser  Asp  Arg  Leu  Gln  Gln
               1010                1015                1020

Ala  Ser  Tyr  Leu  Tyr  Thr  Ser  Arg  Asn  Ala  Val  Gln  Asn  Gly  Asp  Phe
1025                     1030                1035                          1040

Asn  Ser  Gly  Leu  Asp  Ser  Trp  Asn  Thr  Thr  Thr  Asp  Ala  Ser  Val  Gln
               1045                1050                     1055

Gln  Asp  Gly  Asn  Met  His  Phe  Leu  Val  Leu  Ser  His  Trp  Asp  Ala  Gln
               1060                1065                     1070

Val  Ser  Gln  Gln  Leu  Arg  Val  Asn  Pro  Asn  Cys  Lys  Tyr  Val  Leu  Arg
          1075                     1080                1085

Val  Thr  Ala  Arg  Lys  Val  Gly  Gly  Gly  Asp  Gly  Tyr  Val  Thr  Ile  Arg
          1090                     1095                1100

Asp  Gly  Ala  His  His  Gln  Glu  Thr  Leu  Thr  Phe  Asn  Ala  Cys  Asp  Tyr
1105                     1110                1115                          1120

Asp  Val  Asn  Gly  Thr  Tyr  Val  Asn  Asp  Asn  Ser  Tyr  Ile  Thr  Glu  Glu
                    1125                1130                     1135

Val  Val  Phe  Tyr  Pro  Glu  Thr  Lys  His  Met  Trp  Val  Glu  Val  Ser  Glu
               1140                1145                     1150

Ser  Glu  Gly  Ser  Phe  Tyr  Ile  Asp  Ser  Ile  Glu  Phe  Ile  Glu  Thr  Gln
               1155                1160                     1165

Glu   *
1170
```